United States Patent [19]
Sugrue et al.

[11] Patent Number: 5,900,414
[45] Date of Patent: May 4, 1999

[54] METHODS FOR ADMINISTERING INTEGRIN RECEPTOR ANTAGONISTS

[75] Inventors: Michael F. Sugrue, Blue Bell; George D. Hartman, Lansdale; Robert J. Gould, North Wales, all of Pa.

[73] Assignee: Merck & Co., Inc., Rahway, N.J.

[21] Appl. No.: 08/922,836

[22] Filed: Aug. 26, 1997

Related U.S. Application Data

[60] Provisional application No. 60/025,808, Aug. 29, 1996.

[51] Int. Cl.$^6$ .......................... A61K 31/495; A61K 31/50
[52] U.S. Cl. .......................... 514/249; 514/221; 514/300; 514/303
[58] Field of Search ..................... 514/221, 249, 514/300, 303

[56] References Cited

U.S. PATENT DOCUMENTS

| | | | |
|---|---|---|---|
| 5,229,366 | 7/1993 | Tsukada et al. | 514/12 |
| 5,281,585 | 1/1994 | Duggan et al. | 514/79 |
| 5,292,756 | 3/1994 | Duggan et al. | 514/331 |
| 5,470,849 | 11/1995 | Callahan et al. | 514/212 |

FOREIGN PATENT DOCUMENTS

| | | |
|---|---|---|
| 0 710 657 A1 | 5/1996 | European Pat. Off. . |
| WO 94/18981 | 9/1994 | WIPO . |
| WO 95/14683 | 6/1995 | WIPO . |
| WO 97/23451 | 7/1997 | WIPO . |

OTHER PUBLICATIONS

Dahlof et al., Allergy, 42 (3), 215–21, Apr. 1987.
Keenan et al., –Book of Abstract, 211$^{th}$ National Meeting, mar. 24–28 (1996), Medi.–236 ACS code:62PIAJ.

*Primary Examiner*—Raymond Henley, III
*Assistant Examiner*—M. Moezie
*Attorney, Agent, or Firm*—Richard S. Parr; Melvin Winokur

[57] ABSTRACT

The compositions and methods of the invention provide a convenient means for systemically administering an integrin receptor antagonist or a pharmaceutically effective amount thereof to a patient by introducing the antagonist, in an ophthalmic formulation, to the patient's eye.

4 Claims, No Drawings

METHODS FOR ADMINISTERING INTEGRIN RECEPTOR ANTAGONISTS

CROSS-REFERENCE TO RELATED APPLICATION

This application claims the benefit of U.S. provisional application No. 60/025,808, filed Aug. 29, 1996, now abandoned.

BACKGROUND OF THE INVENTION

The invention concerns a means for delivering to a patient a therapeutically effective amount of an integrin receptor antagonist such as a fibrinogen receptor ($\alpha_{IIb}\beta_3$, also referred to as GP IIb/IIIa) antagonist or a vitronectin receptor ($\alpha_v\beta_3$) antagonist.

Integrins constitute an extended family ("superfamily") of membrane receptors interacting with adhesive proteins in plasma and extracellular matrix and with other membrane receptors (counter-receptors). The name "integrin" implies that they integrate the ligands on the outside of the cell with the cytoskeletal apparatus in the inside of the cell. Integrin receptors consist of a noncovalently lined $Ca^{2+}$-dependent, heterodimeric glycoprotein complex composed of $\alpha$ and $\beta$ subunits.

The eight known integrin $\alpha$ subunits give rise to eight families in which one "founder" $\beta$ subunit forms heterodimers with different $\alpha$ subunits. There are at least 14 known $\alpha$ subunits. Among them $\alpha_v$ ("v" stands for association with the vitronectin receptor) seems to be most promiscuous, forming liaisons with six different $\beta$ subunits. Receptors belonging to the $\beta_1$ and $\beta_3$ families are expressed in endothelial cells. The $\beta_1$ family, also named Very Late Antigens (VLA), is represented by the fibronectin receptor ($\alpha_5\beta_1$, or VLA-5), the collagen receptor ($\alpha_2\beta_1$, or VLA-2) and the laminin receptor ($\alpha_6\beta_1$). The $\beta_3$ family is represented by the vitronectin receptor ($\alpha_v\beta_3$), which is structurally similar (the same $\beta_3$ subunit) to the platelet integrin receptor for fibrinogen, glycoprotein IIb–IIIa complex ($\alpha_{IIb}\beta_3$). The functional difference between these two receptors is that the platelet receptor recognizes the $\gamma$ chain domain (HHLGGAKQAGDV) of human fibrinogen and the endothelial vitronectin receptor does not. Both recognize the sequence R-G-D identified as the cell adhesion site of fibronectin, vitronectin, vWf, and the $\alpha$ chain of human fibrinogen. Therefore, synthetic peptides containing the R-G-D sequence cause detachment of endothelial cells from the extracellular in matrix in vitro.

The final obligatory step in platelet aggregation is the binding of fibrinogen to an activated membrane-bound glycoprotein complex, GP IIb/IIIa ($\alpha_{IIb}\beta_3$). Platelet activators such as thrombin, collagen, epinephrine or ADP, are generated as an outgrowth of tissue damage. During activation, GP IIb/IIIa undergoes changes in conformation that result in exposure of occult binding sites for fibrinogen. There are six putative recognition sites within fibrinogen for GP IIb/IIIa and thus fibrinogen can potentially act as a hexavalent ligand to crossing GP IIb/IIIa molecules on adjacent platelets. A deficiency in either fibrinogen or GP IIb/IIIa prevents normal platelet aggregation regardless of the agonist used to activate the platelets. Since the binding of fibrinogen to its platelet receptor is an obligatory component of normal aggregation, GP IIb/IIIa is an attractive target for an antithrombotic agent.

The snake venom proteins, termed disintegrins, have provided important structural information for identifying fibrinogen receptor antagonists, but their antigenicity has limited their development as therapeutic agents (Cook et al. ibid.; and Cox et al. ibid.). Integrilin is a cyclic peptide that is based on the KGD sequence in the snake venom protein barbourin (Cook et al. ibid.; and Cox et al. ibid.). It inhibits ligand binding to GPIIa/IIIa but has very little effect on ligand binding to $\alpha_v\beta_3$. Among the non-peptide compounds are Ro 44-9883 and MK-383, which are administered intravenously, and are also selective for GPIIb/IIIa (Cook et al. ibid.; and Cox et al. ibid.). Orally active agents include SC54684, which is a prodrug (i.e., it requires biotransformation in vivo to its active form) with high oral bioavailability and Ro 43-8857, GR144053, and DMP728, which are themselves the active inhibitors (Cook et al. ibid.; and Cox et al. ibid.). Literally thousands of other compounds have been synthesized in an attempt to obtain optimal potency, metabolic stability, receptor specificity, and favorable intravascular survival. Despite variations in these compounds, virtually of all of them retain the basic charge relations of the RGD sequence with a positive charge separated from a negative charge by approximately 10–20 Å (Cook et al. ibid.; and Cox et al. ibid.).

Since $\alpha_v\beta_3$ is found on endothelial cells, and perhaps smooth muscle cells (Felding-Habermann et al. Curr. Opin. Cell Biol. 1993; 5:864–868), there are many potential sites of action. Recently Choi et al. demonstrated that a peptide that blocks $\alpha_v\beta_3$ prevented intimal hyperplasia after vascular injury in the rat (Choi et al. J. Vasc. Surg. 1994; 19:125–134), and Matsuno et al. demonstrated that a peptide that reacts with GPIIIb/IIIa and $\alpha_v\beta_3$ prevents neointima formation in the hamster (Matsuno et al. Circulation 1994; 90:2203–2206). Whether the peptide used by Choi et al. also inhibited rat platelet GPIIb/IIIa is not known.

Vitronectin (serum spreading factor or S protein) is a 75-kDa glycoprotein found in plasma (500 $\mu$g/mL) and in extracellular matrix, including endothelial cell subendothelium (Barnes et al. J. Biol. Chem. 258; 12548 (1983); Hayman et al. Proc. Natl. Acad. Sci. U.S.A. 80; 4003, (1983); and Preissner et al. Blood 71; 1381 (1986)). Endothelial cells express a surface receptor for vitronectin and bind vitronectin (Fitzgerald et al. Biochemistry 26: 8158 (1987); Cheresh et al. Proc. Natl. Acad. Sci. USA 84; 6471 (1989); Cheng et al. J. Cell Physiol. 139; 275 (1989); Preissner et al. ibid.; and Polack et al. Blood 73; 1519 (1989)). Vitronectin mediates attachment and spreading of endothelial cells, the development of focal adhesion plaques, and clustering of the vitronectin receptor (Dejana et al. Blood 75; 1509 (1990); Dejana et al. J. Cell Biol. 107;1215 (1988); Dejana et al. Blood 71;566 (1988); Charo et al. J. Biol. Chem. 262;9935 (1987); Cheresh et al. Proc. Natl Acad. Sci. USA 84;6471, (1987); Cheng et al. J. Cell Physiol. 139;275 (1989); Barnes et al. J. Biol. Chem. 258:12548 (1983); Hayman et al. J. Cell Biol. 95;20 (1982)). Vitronectin is also found in platelets and is released when platelets are activated; vitronectin then binds to platelets, probably to GP IIIb–IIIa (Barnes et al. Proc. Natl. Acad. Sci. USA 80;1362 (1983)). Vitronectin thus acts as a subendothelial attachment factor for both endothelial cells and platelets. Vitronectin also mediates the adherence of group A and G streptococci to endothelial cells.

Compounds which are $\alpha_v\beta_3$ antagonists are useful for inhibiting bone resorption, treating and preventing osteoporosis, and inhibiting vascular restenosis, diabetic retinopathy, angiogenesis, artherosclerosis and tumor metastasis.

Osteoclasts are multinucleated cells of up to 400 $\mu$m in diameter that resorb mineralized tissue, chiefly calcium carbonate and calcium phosphate, in vertebrates. They are actively motile cells that migrate along the surface of bone. They can bind to bone, secrete necessary acids and proteases and thereby cause the actual resorption of mineralized tissue from the bone.

More specifically, osteoclasts are believed to exist in at least two physiological states. In the secretory state, osteoclasts are flat, attach to the bone matrix via a tight attachment zone (sealing zone), become highly polarized, form a ruffled border, and secrete lysosomal enzymes and acids to resorb bone. The adhesion of osteoclasts to bone surfaces is an important initial step in bone resorption. In the migratory or motile state, the osteoclasts migrate across bone matrix and do not take part in resorption until they attach again to bone.

Integrins are transmembrane, heterodimeric, glycoproteins which interact with extracellular matrix and are involved in osteoclast attachment, activation and migration. The most abundant integrin in osteoclasts (rat, chicken, mouse and human) is the vitronectin receptor, or $\alpha v \beta 3$, thought to interact in bone with matrix proteins that contain the RGD sequence. Antibodies to $\alpha v \beta 3$ block bone resorption in vitro indicating that this integrin plays a key role in the resorptive process. There is increasing evidence to suggest that $\alpha v \beta 3$ ligands can be used effectively to inhibit osteoclast mediated bone resorption in vivo in mammals.

The current major bone diseases of public concern are osteoporosis, hypercalcemia of malignancy, osteopenia due to bone metastases, periodontal disease, hyperparathyroidism, periarticular erosions in rheumatoid arthritis, Paget's disease, immobilization-induced osteopenia, and glucocorticoid treatment.

Additionally, $\alpha v \beta 3$ ligands have been found to be useful in treating and/or inhibiting restenosis (recurrence of stenosis after angioplasty or corrective surgery on the heart valve), artherosclerosis, diabetic retinopathy and angiogenesis (formation of new blood vessels). Moreover, it has been postulated that the growth of tumors depends on an adequate blood supply, which in turn is dependent on the growth of new vessels into the tumor; thus, inhibition of angiogenesis can cause tumor regression in animal models. (See, *Harrison's Principles of Internal Medicine*, 12th ed., 1991). $\alpha v \beta 3$ antagonists, which inhibit angiogenesis, are therefore useful in the treatment of cancer for inhibiting tumor growth. (See e.g., Brooks et al., *Cell*, 79:1157–1164 (1994)).

Oral integrin receptor antagonists are readily absorbed when a patient consumes them on an empty stomach. However, it has been recently observed that absorption and bioavailability of oral integrin receptor antagonists, when taken with food, may be reduced by the presence of food in the stomach. The present compositions and methods provide a means for systemically delivering to a patient therapeutically effective amounts of integrin receptor antagonists.

SUMMARY OF THE INVENTION

The compositions and methods of the invention provide a convenient means for systemically administering an integrin receptor antagonist or a pharmaceutically effective amount thereof to a patient by introducing the antagonist, in an ophthalmic formulation, to the patient's eye. In accordance with the compositions and methods of the invention, the integrin receptor antagonist or a pharmaceutically acceptable salt thereof is formulated, along with suitable carriers, excipients and preservatives, into an ophthalmic preparation. Such preparations include ophthalmic solutions (e.g. eyedrop formulations), ophthalmic suspensions, ophthalmic solid inserts, and ophthalmic ointments.

The invention also includes the use of a fibrinogen receptor antagonist in the manufacture of an ophthalmic medicament for prevention of platelet thrombosis, thromboembolism and reocclusion during and after thrombolytic therapy and prevention of platelet thrombosis, thromboembolism and reocclusion after angioplasty or coronary artery bypass procedures, to treat patients with unstable angina, and to prevent subsequent myocardial infarction.

The invention also includes the use of a vitronectin receptor antagonist in the manufacture of an ophthalmic medicament for treating inflammation, cancer, atherosclerosis, restenosis, osteoporosis, hyperparathyroidism, Paget's disease, malignant hypercalcemia, metastatic osteolytic lesions, and bone loss.

The invention also includes the use of a compound which inhibits the binding of fibrinogen to the glycoprotein IIb/IIIa receptor, or a pharmaceutically acceptable salt thereof, or a compound which inhibits the binding of vitronectin to the $\alpha_v \beta_3$ receptor, or a pharmaceutically acceptable salt thereof, in the manufacture of an ophthalmic medicament for reducing the risk of acute coronary ischemic syndrome, or inhibiting osteoclast cellular adhesion, solubilization of mammalian bone minerals by osteoclast cells, inhibiting diabetic retinopathy, or inhibiting macular degeneration in a mammal.

DETAILED DESCRIPTION OF THE INVENTION

In eyedrop formulations, from about 0.01–5.0% (w/v) of active ingredient can be employed. In one class of eyedrop formulations, from about 0.01–2.0% (w/v) of active ingredient can be employed. In a subclass of the class, from about 0.1–1.0% (w/v) of active ingredient can be employed. Suitable eyedrop volume is, for example, 20, 30, 35, 50 or 100 $\mu$l. The objective is to administer a dose of between about 0.005–0.5 mg/kg per day to each eye, for a total dosage of between about 0.01–1.0 mg/kg/day, e.g. a dose of about 0.05 mg/kg per day to each eye, for a total dosage of about 0.1 mg/kg/day. For example, the eyedrops can be used to provide doses of 1 mg, 10 mg, or 50 mg. These dosage values are based on known and presently understood pharmacology of the integrin receptor antagonists, Dosage requirements are variable and must be individualized on the basis of the disease and the response of the patient.

Suitable eyedrop formulations are those which are isotonic and maintain sufficient contact with the eye surface to systemically deliver the active agent to the patient. Such formulations advantageously have a pH approximating neutrality and are non-irritating to the eye, e.g. they do not induce tearing and consequential flow of active agent out of the eye. Pharmaceutically acceptable carriers are, for example, water, mixtures of water and water-miscible solvents such as lower alkanols or arylalkanols, vegetable oils, polyalkylene glycols, petroleum based jelly, ethyl cellulose, hydroxy ethyl cellulose, ethyl oleate, carboxymethylcellulose, polyvinylpyrrolidone, isopropyl myristate and other conventionally-employed non-toxic, pharmaceutically acceptable organic and inorganic carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1000, 1500, 4000, 6000 and 10000, antibacterial compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like.

In the procedure for making eyedrops, formulations are rendered sterile by appropriate means, such as starting the preparation procedure with sterile components and proceeding under sterile conditions, irradiating or autoclaving the finished formulation, and the like. Suitable anti microbial agents are also useful for maintaining sterility of the eyedrop.

The ophthalmic preparation may also be an ophthalmic solid insert such as one which, after dispensing the integrin receptor antagonist, remains essentially intact, or a bioerodible insert that is soluble in lacrimal fluids, or otherwise disintegrates. For example, one may use a solid water soluble polymer as the carrier for the integrin receptor antagonist. The polymer used to form the insert may be any water soluble non-toxic polymer, for example, cellulose derivatives such as methylcellulose, sodium carboxymethyl cellulose, hydroxyethylcellulose, hydroxypropylcellulose, hydroxypropylmethyl cellulose, acrylates such as polyacrylic acid salts, ethylacrylates, polyacrylamides, natural products such as gelatin, alginates, pectins, tragacanth, karaya, chondrus, agar, acacia, starch derivatives such as starch acetate, hydroxyethyl starch ethers, hydroxypropyl starch, as well as other synthetic derivatives such as polyvinyl alcohol, polyvinyl pyrrolidone, polyvinyl methyl ether, polyethylene oxide, neutralized carbopol, gellan gum and xanthan gum, and mixtures of said polymers.

The ophthalmic preparation may also be an ophthalmic ointment which is compounded, for example, by mixing finely milled powdered ingredients with a small amount of white petrolatum and levigating or otherwise mixing until a uniform distribution is achieved. The balance of white petrolatum is added by geometric addition until the desired dosage form is made.

Integrin receptor antagonists suitable for administration using compositions of the invention include fibrinogen receptor antagonists and vitronectin receptor antagonists.

Antagonists for the glycoprotein IIb/IIIa fibrinogen receptor have been described in, for example, U.S. Pat. Nos. 5,470,849, 5,463,011, 5,455,243, 5,451,578, 5,446,056, 5,441,952, 5,422,249, 5,416,099, 5,405,854, 5,397,791, 5,393,760, 5,389,631, 5,380,713, 5,374,622, 5,358,956, 5,344,783, 5,340,798, 5,338,7235,334,596, 5,321,034, 5,318,899 (e.g. cyclic heptapeptides Mpr-(Acetimidyl-Lys)-Gly-Asp-Trp-Phe-Cys-$NH_2$, Mpr-(Acetimidyl-Lys)-Gly-Asp-Trp-Phe-Pen-$NH_2$, Mpr-(Phenylimidyl-Lys)-Gly-Asp-Trp-Phe-Pen-$NH_2$, and Mpr-(Phenylimidyl-Lys)-Gly-Asp-Trp-Phe-Cys-$NH_2$, wherein Mpr is mercapto propionyl), U.S. Pat. Nos. 5,312,923, 5,294,616, 5,292,756 (e.g. 2-S-(n-Butylsulfonylamino)-3[4-piperidin-4-yl)butyloxyphenyl] propionic acid hydrochloride), U.S. Pat. Nos. 5,281,585 5,272,158, 5,264,420, 5,260,307, 5,239,113 (e.g. Ethyl 3-[[4-[[4-(aminoiminomethyl)phenyl]amino]-1,4-dioxobutyl]amino]-4-pentynoate), U.S. Pat. Nos. 5,227,490, 5,206,373, 4,703,036 (e.g. N-Methyl-D-phenylalanyl-N-[(1S)-1-formyl-4-guanidinobutyl]-L-prolinamide), EP 505 868 (e.g. ((1-(2-((4(aminoiminomethyl)benzoyl)amino)-3-(4-hydroxyphenyl)-1-oxopropyl)-4-piperidinyl)oxy)-(S)-acetic acid), WO 9311152 (e.g. N-(2-(2-(((3-((aminoiminomethyl)amino)propyl)amino)-carbonyl)-1-piperidnyl)-1-(cyclohexylmethyl)-2-oxoethyl)-(R,S)-glycine), WO 9418981 (e.g. 2(S)-[(p-Toluenesulfonyl) amino]-3-[[[5,6,7,8-tetrahydro-4-oxo-5-[2-(piperidin-4-yl) ethyl]-4H-pyrazolo-[1,5-a][1,4]diazepin-2-yl]carbonyl]-amino]propionic acid), WO 9514683 (e.g. methyl-$N^3$-[2-{3-(4-formamidinophenyl)-isoxazolin-5(R)-yl}-acetyl]-$N^2$-(n-butyloxycarbonyl)-2,3-(S)-diaminopropionate acetate salt), EP 333 356 and WO 9422820. They are described as useful for inhibiting fibrinogen binding and inhibiting clot formation.

Antagonists for the $\alpha_v\beta_3$ vitronectin receptor have been described in, for example, WO 9723451, WO 9708145, Japanese Patent 6128289, WO 9600730, WO 9600574, and U.S. Pat. No. 5,229,366. These are generally described as useful for treating inflammation, cancer, atherosclerosis, restenosis, osteoporosis, hyperparathyroidism, Paget's disease, malignant hypercalcemia, metastatic osteolytic lesions, and bone loss.

Antagonists for integrin receptors that are described as useful for treating thrombosis and osteoporosis are described in, for example, European Publications 710 657, 683 173, 741 133, 668 278, 645 376, 643 072, 623 615 in WO 9532710, WO 9701549, WO 9626190, WO 9606087, WO 9523811, U.S. Pat. No. 5,565,449, and Japanese Patent 7206860.

Glycoprotein IIb/IIIa receptor antagonists and their pharmaceutically acceptable salts, and $\alpha_v\beta_3$ receptor antagonists and their pharmaceutically acceptable salts, are useful in the present invention. The term "pharmaceutically acceptable salts" means non-toxic salts of the compounds which include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, valerate.

Pharmaceutically effective amounts of the glycoprotein IIb/IIIa receptor antagonists and the $\alpha_v\beta_3$ receptor antagonists are suitable for use in the compositions and methods of the present invention. The term "pharmaceutically effective amount" means that amount of a drug or pharmaceutical agent that will elicit the biological or medical response of a tissue, system or animal that is being sought by a researcher or clinician.

The compositions and methods of the present invention comprising fibrinogen receptor antagonists are useful in combination with procedures for treating patients with other anticoagulants (e.g. thrombin inhibitors such as heparin and Factor Xa inhibitors such as warfarin), thrombolytic agents (e.g. streptokinase and tissue plasminogen activator), and platelet antiaggregation agents (e.g. aspirin and dipyridamole).

The fibrinogen receptor antagonist may be administered to patients where prevention of thrombosis by inhibition of binding of fibrinogen to the platelet membrane glycoprotein complex IIb/IIIa receptor is desired. Such administration is useful in surgery on peripheral arteries (arterial grafts, carotid endarterectomy), in cardiovascular surgery where manipulation of arteries and organs, and/or the interaction of platelets with artificial surfaces, leads to platelet aggregation and potential formation of thrombi and thromboemboli, and for treating patients where inhibition of human or mammalian acute coronary ischemic syndrome is desired. The aggregated platelets may form thrombi and thromboemboli. The fibrinogen receptor antagonists may be administered to these surgical patients to prevent the formation of thrombi and thromboemboli.

Other applications of the fibrinogen receptor antagonists include prevention of platelet thrombosis, thromboembolism and reocclusion during and after thrombolytic therapy and prevention of platelet thrombosis, thromboembolism and reocclusion after angioplasty or coronary artery bypass procedures. It may also be used to treat patients with unstable angina and prevent subsequent myocardial infarction.

The compositions and methods of the present invention comprising vitronectin receptor antagonists elicit an $\alpha_v\beta_3$ antagonizing effect in a mammal in need thereof. The $\alpha_v\beta_3$ antagonizing effect is, for example, inhibition of bone resorption, inhibition of restenosis, inhibition of artherosclerosis, inhibition of angiogenesis, inhibition of diabetic retinopathy or inhibition of tumor growth.

The compositions and methods of the present invention comprising vitronectin receptor antagonists are useful for treating and/or preventing a condition mediated by an $\alpha_v\beta_3$ receptor in a mammal in need thereof, such as osteoporosis, cancer, bone resorption, restenosis, diabetic retinopathy, artherosclerosis, angiogenesis or tumor growth.

The compositions and methods of the present invention comprising vitronectin receptor antagonists are useful for treating hypercalcemia of malignancy, osteopenia due to bone metastases, periodontal disease, hyperparathyroidism, periarticular erosions in rheumatoid arthritis, Paget's disease, and immobilization-induced osteopenia.

The dosage regimen is selected in accordance with a variety of factors including type, species, age, weight, sex and medical condition of the patient; the severity of the condition to be treated; the renal and hepatic function of the patient; and the particular compound or salt thereof employed. An ordinarily skilled physician or veterinarian can readily determine and prescribe the effective amount of the drug required to prevent, counter, or arrest the progress of the condition.

EXAMPLE 1

Eye Drops

Solution compositions for topical administration containing 0.64% w/v 2(S)-[(p-Toluenesulfonyl)amino]-3-[[[5,6,7,8-tetrahydro-4-oxo-5-[2-(piperidin-4-yl)ethyl]-4H-pyrazolo-[1,5-a][1,4]diazepin-2-yl]carbonyl]-amino] propionic acid (compound 1—1) are prepared as illustrated below:

| | |
|---|---|
| Compound 1-1 | 6400 mg |
| 0.5% hydroxyethylcellulose | 1 L |

Compound 1—1 was dissolved directly into 0.5% hydroxyethylcellulose to form a solution. The formulation was rendered sterile by starting the preparation procedure with sterile components and proceeding under sterile conditions.

EXAMPLE 2

Eye Drops

Additional eyedrop formulations are prepared having the following composition:

| | |
|---|---|
| Compound 1-1 | 0.5% |
| Benzalkonium chloride solution | 0.02% v/v |
| Disodium edetate | 0.05% |
| NaCl | 0.8% |
| Water | to 100% |

EXAMPLE 3

Ophthalmic Inserts

Ophthalmic inserts are manufactured from compression molded films which are prepared on a Carver Press by subjecting the powdered mixture of 1 mg Compound 1—1 and 12 mg hydroxymethylcellulose to a compression force of 12,000 lbs. (gauge) at 300 degrees F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R.H. at 30 degrees C.) for two or four days. After removal from the humidity cabinet, the vials are stoppered from the humidity cabinet, the vials are stoppered and then capped. The vials containing the hydrate insert are then autoclaved at 250 degrees F. for one-half hour.

EXAMPLE 4

Eyedrop Administration

One drop (100 μl) of the eyedrop prepared in Example 1 was instilled into each eye of a conscious purpose-bred mongrel dog (HHCMLH). Ex vivo inhibition of platelet aggregation as compared to baseline predose aggregatory response induced by 10 μM ADP+1 μM epinephrine was measured over a period of 4 hours and shown to achieve over 50% inhibition:

| Time (minutes) | % Inhibition |
|---|---|
| 0 | 0 |
| 1 | 9 |
| 5 | — |
| 15 | 20 |
| 30 | 14 |
| 45 | 14 |
| 60 | 20 |
| 75 | 39 |
| 90 | 8 |
| 120 | 42 |
| 180 | 30 |
| 240 | 57 |

EXAMPLE 5

Eyedrop Administration

One drop (100 μl) of the eyedrop prepared in Example 1 was instilled into each eye of a conscious purpose-bred mongrel dog (HIAMGV). Ex vivo inhibition of platelet aggregation as compared to baseline predose aggregatory response induced by 10 μM ADP+1 μM epinephrine was measured over a period of 4 hours and shown to achieve 100% inhibition:

| Time (minutes) | % Inhibition |
| --- | --- |
| 0 | 0 |
| 1 | 16 |
| 5 | 32 |
| 15 | 6 |
| 30 | 38 |
| 45 | 30 |
| 60 | 68 |
| 75 | 78 |
| 90 | 62 |
| 120 | 68 |
| 180 | 88 |
| 240 | 100 |

EXAMPLE 6

Eyedrop Administration

One drop (100 μl) of the eyedrop prepared in Example 1 was instilled into each eye of a conscious purpose-bred mongrel dog (41309). Ex vivo inhibition of platelet aggregation as compared to baseline predose aggregatory response induced by 10 μM ADP+1 μM epinephrine was measured over a period of 24 hours and shown to achieve 100% inhibition:

| Time (minutes) | % Inhibition |
| --- | --- |
| 0 | 0 |
| 30 | 84 |
| 60 | 74 |
| 90 | 90 |
| 120 | 90 |
| 180 | 100 |
| 240 | 87 |
| 300 | 100 |
| 360 | 100 |
| 420 | 100 |
| 480 | 100 |
| 1440 | 88 |

EXAMPLE 7

Eyedrop Administration

One drop (100 μl) of the eyedrop prepared in Example 1 was instilled into each eye of a conscious purpose-bred mongrel dog (HGFMKC). Ex vivo inhibition of platelet aggregation as compared to baseline predose aggregatory response induced by 10 μM ADP+1 μM epinephrine was measured over a period of 24 hours and shown to achieve over 50% inhibition:

| Time (minutes) | % Inhibition |
| --- | --- |
| 0 | 0 |
| 30 | 2 |
| 60 | 19 |
| 90 | 22 |
| 120 | 8 |
| 180 | 31 |
| 240 | 23 |
| 300 | 43 |
| 360 | 57 |
| 420 | 41 |
| 480 | 49 |
| 1440 | 56 |

What is claimed is:

1. A method for administering an integrin receptor antagonist to a patient in need of such antagonist comprising topically applying to the patient's eye an effective amount of a composition comprising a carrier suitable for topical ophthalmological administration and between about 0.01–5% w/v of an integrin receptor antagonist or a pharmaceutically acceptable salt thereof or a prodrug thereof.

2. A method for inhibiting platelet aggregation in a patient comprising topically applying to the patient's eye an effective amount of the composition comprising a carrier suitable for topical ophthalmological administration and between about 0.01–5% w/v of a fibrinogen receptor antagonist or a pharmaceutically acceptable salt thereof or a prodrug thereof.

3. A method for reducing the risk of acute coronary ischemic syndrome in patients at risk to acute coronary ischemic syndrome comprising topically applying to the patient's eye a safe and effective amount of a glycoprotein IIb/IIIa receptor antagonist composition comprising a carrier suitable for topical ophthalmological administration and between about 0.01–5% w/v of a glycoprotein IIb/IIIa receptor antagonist or a pharmaceutically acceptable salt thereof or a prodrug thereof.

4. A method for inhibiting bone resorption, inhibiting restenosis, inhibiting angiogenesis, inhibiting diabetic retinopathy or inhibiting tumor growth in a patient comprising topically applying to the patient's eye a therapeutically effective amount of a composition comprising a carrier suitable for topical ophthalmological administration and between about 0.01–5% w/v of a vitronectin receptor antagonist or a pharmaceutically acceptable salt thereof or a prodrug thereof.

* * * * *